(12) United States Patent
Hergert

(10) Patent No.: US 8,173,183 B2
(45) Date of Patent: May 8, 2012

(54) MUCOSAL MEMBRANE HEALANT AND MOISTURIZER

(76) Inventor: Carmell Hergert, Groves, TX (US)

( * ) Notice: Subject to any disclaimer, the term of this patent is extended or adjusted under 35 U.S.C. 154(b) by 124 days.

(21) Appl. No.: 12/166,672

(22) Filed: Jul. 2, 2008

(65) Prior Publication Data

US 2010/0003352 A1   Jan. 7, 2010

(51) Int. Cl.
*A61K 36/886* (2006.01)

(52) U.S. Cl. ........ 424/744; 424/725; 424/774; 424/401; 514/458

(58) Field of Classification Search .................. None
See application file for complete search history.

(56) References Cited

U.S. PATENT DOCUMENTS

| | | | |
|---|---|---|---|
| 5,266,318 A * | 11/1993 | Taylor-McCord | 424/744 |
| 5,376,365 A | 12/1994 | Dikstein | |
| 5,897,872 A * | 4/1999 | Picciano | 424/434 |
| 5,908,865 A | 6/1999 | Doi et al. | |
| 6,080,783 A | 6/2000 | Davidson et al. | |
| 6,482,442 B1 * | 11/2002 | Dado | 424/539 |
| 6,579,516 B1 * | 6/2003 | Mansouri | 424/70.1 |
| 6,620,852 B2 * | 9/2003 | Brogan et al. | 514/626 |
| 6,673,835 B1 | 1/2004 | Hensley et al. | |
| 6,867,238 B2 * | 3/2005 | Schrauzer | 514/706 |
| 6,869,623 B2 | 3/2005 | Viamonte, Jr. et al. | |
| 6,949,262 B1 | 9/2005 | Smothers | |
| 2002/0125271 A1 * | 9/2002 | Zeitlin | 222/181.3 |
| 2003/0059440 A1 | 3/2003 | Clarot et al. | |
| 2005/0019431 A1 | 1/2005 | Modak et al. | |
| 2005/0118243 A1 | 6/2005 | Hensley et al. | |
| 2005/0180924 A1 | 8/2005 | Clarot et al. | |
| 2007/0003632 A1 * | 1/2007 | Lapointe | 424/539 |
| 2007/0265337 A1 | 11/2007 | Hensley et al. | |
| 2009/0130048 A1 * | 5/2009 | Oronsky et al. | 424/78.02 |

* cited by examiner

*Primary Examiner* — Susan Hoffman
(74) *Attorney, Agent, or Firm* — John C. Cave; Gunn, Lee & Cave, PC

(57) ABSTRACT

A pharmaceutical composition for treatment and prevention of severely dehydrated soft tissue is disclosed. The pharmaceutical composition has ingredients that prevent the onset of dehydration and ingredients that increase the healing rate of dehydrated tissue that has become cracked. In particular, the present invention treats and prevents the dry-nose condition caused in oxygen respiratory therapy.

2 Claims, No Drawings

MUCOSAL MEMBRANE HEALANT AND MOISTURIZER

CROSS REFERENCES TO RELATED APPLICATIONS

None.

STATEMENT REGARDING FEDERALLY SPONSORED RESEARCH OR DEVELOPMENT

Not applicable.

BACKGROUND OF THE INVENTION

In the field of respiratory therapy, patients often undergo oxygen therapy treatment to alleviate symptoms associated with respiratory ailments. Oxygen therapy is a therapeutic technique in which pure oxygen is continuously administered to a patient so that every time the patient takes a breath, the pure oxygen enters into the patient's lungs. For the majority of cases, the oxygen is delivered to the lungs through the nose, by a nasal cannula inserted into the patient's nostril. By delivering the oxygen through the nose, patients can use their mouth without interference from the oxygen. As a result, patients can eat, drink, or talk while receiving oxygen. Although the nasal-delivered oxygen is helpful for the respiratory condition, the continuous stream of gas through the patient's nostril and nasal cavity causes them to severely dry out. In prolonged oxygen therapy, the soft, moist tissue in the patient's nostril and nasal cavity may become severely dehydrated and cracked. Many times, these cracks are so severe that patients will bleed from them.

The so-called "dry-nose condition," which is extremely uncomfortable and oftentimes painful, creates a dilemma for patients by forcing them to choose between the lesser of two evils. On the one hand, a patient can receive oxygen to treat his/her respiratory ailment but suffer the effects of the dry-nose condition. On the other hand, the patient can forego the oxygen therapy to prevent the dry-nose condition but suffer the debilitating symptoms of their respiratory ailment. Either way, patients are in a no win situation.

To combat the dry-nose condition, it is common in the art for patients to topically apply an over-the-counter, water-based lubricant to the interior walls of the nostril and nasal cavity. These lubricants are normally found in gel form. For example, one water-based gel that is commonly used for treating the dry-nose condition is a product marketed under the name K-Y Jelly®. It has been found that applying K-Y Jelly® will lubricate the soft tissue on the nasal cavity walls and the interior of the nostril. This lubrication helps retain moisture and prevents the cracks from forming. However, being water-based, K-Y Jelly®, as well as other water-based lubricants, evaporates very quickly. This consequence is further exacerbated by the steady stream of oxygen coming from the cannula and continuously passing over the gel once it is applied. As a result, patients must repeatedly remove the cannula from their nose and reapply this product. Furthermore, the water-based gels do not heal existing cracks in the soft tissue.

SUMMARY OF THE INVENTION

The present invention is directed to creating a more effective, longer lasting pharmaceutical composition for treating the dry-nose condition. In this regard, the pharmaceutical composition has ingredients in it that prevent rapid evaporation of the composition once applied to the interior walls of the nostrils and the nasal cavity. Once applied, the present invention binds to the interior walls and lasts longer than existing treatments known in the art. In addition, the present invention also contains ingredients that aid the body's natural healing processes. As a result, existing cracks that have manifested as a result of the dry-nose condition heal quicker with the present invention.

It is the object of the present invention to create an effective pharmaceutical composition for treating the dry-nose condition. In keeping with this objective, the present invention effectively lubricates and moisturizes the soft tissue within the nostrils and the nasal cavity to prevent the initial onset of the dry-nose condition. Additionally, as a further preventative measure, the present invention binds to the interior of the nostrils and the nasal cavity to create a barrier between the soft tissue and the stream of oxygen coming from the nasal cannula. It is a further object of the pharmaceutical composition of the present invention to effectively heal existing cracks that have been formed in dehydrated nasal soft tissue and to act as an antiseptic to these cracks.

In furtherance of the above-mentioned objects of the present invention, the pharmaceutical composition created is an improvement over the water-based gel treatments known in the art. Once applied, the present invention adheres to the nasal soft tissue for a much longer period than the water-based gels currently used to treat the dry-nose condition, making the present invention more effective. In this regard, because the present invention is specifically formulated to decrease evaporation, it stays in contact with the affected portions of the nostrils and the nasal cavity for a longer period of time. As a result, the beneficial objects discussed above have more time to achieve their intended result and the composition does not have to be reapplied as often as the water-based gels known in the art.

BRIEF DESCRIPTION OF THE DRAWINGS

None.

DETAILED DESCRIPTION OF THE INVENTION

The starting point for the present invention is a water-based gel known in the art to help alleviate the symptoms of the dry-nose condition. The water-based gel is marketed by Fougera® under the trade name Surgilube®. Surgilube® consists of water, propylene oxide chlorhexidine gluconate 20%, acetic acid, lavender, propylene glycol, hydroxypropyl methylcellulose, polypropylene glycol, and sodium acetate. In its normal use, Surgilube® provides lubrication to facilitate catheter insertion, insertion of surgical instruments, and insertion of magic bullet suppositories as well as gloves into orifices in the body.

Aside from its lubricating properties, Surgilube® is beneficial in that its active ingredient, chlorhexidine gluconate 20%, has antimicrobial properties. Not only does the chlorhexidine gluconate 20% inhibit the growth and reproduction of microorganisms, it actually kills existing microorganisms present on the devices and/or skin that the Surgilube® comes into contact with. As part of the present invention, when applied to the interior nasal soft tissue, the Surgilube® acts as an antiseptic vis-à-vis the chlorhexidine gluconate 20%. That is, the Surgilube® reduces the possibility of infection by destroying microorganisms thriving in the cracked soft tissue of severely dehydrated nostrils and/or a severely dehydrated nasal cavity.

Added to the Surgilube®, the next ingredient of the present invention is a preservative agent. The presence of the preservative agent in the pharmaceutical composition of the present invention keeps the composition intact and increases the shelf life of the present invention. Acting as an antioxidant, the preservative agent prevents oxidation of the ingredients found in the Surgilube®, as well as the other ingredients in the pharmaceutical composition of the present invention. In this regard, the preservative agent prevents molecules from losing electrons through oxidative processes, and helps maintain the molecular structure of the pharmaceutical composition.

Furthermore, the preservative agent helps protect the body's cells from degeneration caused by harmful free radicals produced during oxidative processes. The existence of free radicals, which are highly reactive, often starts molecular chain reactions that harmfully affect cell structure and may ultimately kill the cell. For example, the harmful effect of oxidation on cells, which is termed oxidative stress, can damage cellular components such as DNA, proteins, and lipids. As such, soft tissue cells that are reproducing to heal the cracks in the soft tissue of the nostrils and nasal cavity may be affected through oxidative stress and prolong the healing process.

In the preferred embodiment, the preservative agent for the present invention is tocopheryl acetate. Tocopheryl acetate is the ester of acetic acid and tocopherol, also known as Vitamin E. Less acidic than tocopherol, tocopheryl acetate is an analog of tocopherol but is more stable than tocopherol alone. In this regard, tocopheryl acetate is less susceptible to oxidative destruction and provides for a slightly better shelf life than tocopherol. In other words, tocopheryl acetate has better preservative characteristics than tocopherol.

Another embodiment of the present invention utilizes a grapefruit seed extract (GSE) and vegetable glycerin mixture as the preservative agent. In this embodiment, it was found that a 60% to 40% ratio by volume of GSE to vegetable glycerin works well. That is, 60% by volume of the preservative agent is GSE and 40% by volume of the preservative agent is vegetable glycerine. The percentages are calculated based on a total volume of the preservative agent present in the pharmaceutical composition.

The next ingredient in the preferred embodiment of the present invention is a healing agent that promotes wound healing for humans by increasing the growth rate for those cells associated with wound healing. Applied to the present invention, in those patients where the soft tissue of the nostrils and the nasal cavity has become dehydrated and cracked, the healing agent stimulates the growth of epithelial cells and/or fibroblasts on this tissue.

In the preferred embodiment of the present invention, the healing agent is aloe barbadensis leaf extract. Aloe barbadensis leaf extract is an extract from the leaves of the plant species aloe barbadensis. Also known as aloe vera, aloe barbadensis's leaves consist of two parts: (1) the pericyclic cells found just below the plant's outer surface and (2) the inner area of the leaf where the gel resides. Well known for its medicinal value, the inner gel of the aloe barbadensis leaf is the desired portion of the leaf for purposes of a healing agent. In contrast, the pericyclic cells, which produce a bitter, yellow latex containing anthraquinones, can be used for laxatives but must be eliminated through manufacturing processes designed to extract the gel and its associated healing properties.

Manufacturing processes for isolating the gel are varied and well known in the art. Most processes involve either (1) filleting the leaf and only using certain portions or (2) processing the entire leaf. In the first instance, the leaf is filleted to remove the green skin and the outer layers of gel. After filleting, the inner layer of gel remains. Care must be taken to ensure that the green skin, or rind, does not contaminate the remaining gel, and once isolated additional steps must be taken to stabilize the inner gel. In contrast, some manufacturers use the whole leaf to increase the yield of extract. After washing the cut leaves, these manufacturers grind up the entire leaf and incorporate steps to remove the unwanted anthraquinones. Although this second type of processing adds manufacturing costs, the yield can be increased five to six time over the first type, though the final product is considered inferior.

Though alternative embodiments of the pharmaceutical composition can be formulated without it, in the preferred embodiment of the present invention a base oil is present. Base oils, also known as carrier oils or vegetable oils, are oils derived from plants and mainly consist of triglycerides. Triglycerides are glycerides where the glycerol is esterified with three fatty acids. Traditionally, base oils are extracted from plants by mechanically pressing certain parts of the plant until the oil seeps out. Though other portions of the oil-producing plants may yield oil, usually it is the plants' seeds that are pressed.

The essential function of the base oil is to maintain the other ingredients at the location where the pharmaceutical composition was applied. In this regard, the base oil is not easily absorbed into the skin or soft tissue of the nostrils or the nasal cavity. Instead, it remains on the surface of the site being treated with the pharmaceutical composition while other ingredients are absorbed into the treatment site. By remaining on the surface of the treatment site, the base oil helps combat evaporation of the other ingredients that are mixed into it. Thus, the base oil allows the other ingredients to perform their functions for longer periods of time.

In the preferred embodiment, the base oil is safflower oil. Safflower oil is an extremely safe base oil that is non-toxic, so much so that it can even be ingested by humans and is sometime taken as a nutritional supplement. Safflower oil is a thin oil that is both flavorless and colorless. Other base oils that have been shown to be effective are grape seed oil and sesame oil.

The pharmaceutical composition of the present invention is a mixture of the above-named ingredients. There are no known chemical reactions between the ingredients. To produce the pharmaceutical composition of the present invention, the Surgilube® is the starting point with the other ingredients added. While these other ingredients are being added, the mixture is continuously stirred, at room temperature. After mixing, the pharmaceutical composition is in gel form.

The above-described pharmaceutical composition is applied to the nostrils and/or the nasal cavity using an applicator tip, such as a cotton swab. The applicator tip will be inserted into the nostrils and into the nasal cavity through the nostrils. As a result, all obstructions at the nostrils should be removed. For example, the nasal cannula should be temporarily taken out of the nostril in treating the dry-nose condition caused by oxygen delivery through nasal cannula. An amount of composition is placed on the applicator tip, the applicator tip is inserted into the nostrils up to a desired point, and the applicator tip is moved about the surface of the soft tissue affected with the dry-nose condition in manner so as to deposit an effective amount of the pharmaceutical composition on the interior wall. An effective amount is the amount of pharmaceutical composition required to cover the affected areas.

Once applied, the pharmaceutical composition will adhere to the interior wall of the nostrils and nasal cavity and the nasal cannula can be reinserted into the nostrils. While the nasal cannula is in place, the pharmaceutical composition will stay adhered to the soft tissue, acting as a barrier between the oxygen and the soft tissue to prevent further dehydration, as well as healing the existing cracks of the current dry-nose condition. After the nasal cannula has been reinserted, the present invention's resistance to evaporation will enable the pharmaceutical composition to remain in place for a long period of time.

The present invention can also be embodied in a spray form, where normal saline is added to the mixture. Normal saline, which is well known in the medical arts, is a water-based solution with a 0.9% weight/volume percentage of sodium chloride (NaCl) as the solute. Normal saline is non-toxic and is commonly used in intravenous drips (IVs) for treating severe dehydration, when liquids cannot be taken orally. In the present invention the normal saline acts to dilute the other ingredients, putting the pharmaceutical composition in a more liquid, less viscous form. With reduced viscosity, the pharmaceutical composition can be sprayed through the nostrils into the nasal cavity. The composition still retains characteristics that enable it to remain in the nasal cavity for long periods of time. Although the normal saline will evaporate quickly, the other ingredients will remain adhered to the soft tissue of the nasal cavity.

To formulate the pharmaceutical composition of the present invention, the specific amount of each ingredient is best expressed using the percentage by volume of total volume for each ingredient, keeping in mind that the pharmaceutical composition will have a definable total volume after all the ingredients are mixed. The exact amount of each ingredient varies, depending on the physical form of the present invention. For example, the percentage amount of each ingredient present in the gel form varies from the percentage amount of each ingredient present in the spray form. Moreover, the percentage amount of each ingredient in the gel form without the base oil differs from the percentage amount of each ingredient present in the gel form with the base oil.

The amount of each ingredient within each physical form of the present invention also ranges. In this regard, preferred embodiments exist within each physical form and specific volume percentages of each ingredient are known. These preferred embodiments contain specific percentages of each ingredient and are known to achieve the objects of the present invention most effectively. However, alternative embodiments also exist within each physical form of the present invention. These alternative embodiments still function to achieve the desired objects of the present invention, but are not as effective as the preferred embodiments. For example, the pharmaceutical composition in an alternative embodiment may not adhere to the soft issue of the nostrils and the nasal cavity as effectively as the preferred embodiment. Or, the pharmaceutical composition in an alternative embodiment may not resist evaporation as long as the preferred embodiment. Regardless of these inferior characteristics, alternative embodiments within each physical form of the present invention do exist, and the percentage volume of the ingredients for each physical form ranges.

In the gel form of the pharmaceutical composition without the base oil, the percentage volume of each ingredient is as follows: (a) Surgilube®—between 70% and 99% by volume of the total volume of pharmaceutical composition; (b) preservative agent—between 0.1% and 10% by volume of the total volume of pharmaceutical composition; and, (c) healing agent—between 0.1% and 20% by volume of the total volume of pharmaceutical composition.

In the preferred embodiment of the gel form without the base oil, the specific amount of each ingredient is as follows: (a) Surgilube®—93.75% by volume of the total volume of pharmaceutical composition; (b) preservative agent—3.125% by volume of the total volume of pharmaceutical composition; and, (c) healing agent—3.125% by volume of the total volume of pharmaceutical composition in this form. Each of these numbers is expressed by rounding to the nearest one thousandth of a percent. Furthermore, in the preferred embodiment of this form the preservative agent is tocopheryl acetate and the healing agent is aloe barbadensis leaf extract.

In the gel form of the pharmaceutical composition that does contain the base oil, the percentage volume of each ingredient is as follows: (a) Surgilube®—between 40% and 99% by volume of the total volume of pharmaceutical composition; (b) preservative agent—between 0.1% and 10% by volume of the total volume of pharmaceutical composition; (c) healing agent—between 0.1% and 20% by volume of the total volume of pharmaceutical composition; and, (d) base oil—between 0.1% and 30% by volume of the total volume of pharmaceutical composition.

In the preferred embodiment of the gel form that does contain the base oil, the specific amount of each ingredient is as follows: (a) Surgilube®—90.91% by volume of the total volume of pharmaceutical composition; (b) preservative agent—3.03% by volume of the total volume of pharmaceutical composition; (c) healing agent—3.03% by volume of the total volume of pharmaceutical composition in this form; and, (d) base oil—3.03% by volume of the total volume of pharmaceutical composition. Each of these numbers is expressed by rounding to the nearest one hundredth of a percent. Furthermore, in the preferred embodiment of this form the preservative agent is tocopheryl acetate, the healing agent is aloe barbadensis leaf extract, and the base oil is safflower oil.

In the spray form of the pharmaceutical composition, the percentage volume of each ingredient is as follows: (a) Surgilube®—between 10% and 40% by volume of the total volume of pharmaceutical composition; (b) preservative agent—between 0.1% and 2.5% by volume of the total volume of pharmaceutical composition; (c) healing agent—between 0.1% and 2.5% by volume of the total volume of pharmaceutical composition; (d) base oil—between 0.1% and 5.0% by volume of the total volume of pharmaceutical composition; and, (e) normal saline solution—between 50% and 85% by volume of the total volume of pharmaceutical composition.

In the preferred embodiment of the spray form, the specific amount of each ingredient is as follows: (a) Surgilube®—20.41% by volume of the total volume of pharmaceutical composition; (b) preservative agent—1.02% by volume of the total volume of pharmaceutical composition; (c) healing agent—1.02% by volume of the total volume of pharmaceutical composition; (d) base oil—1.02% by volume of the total volume of pharmaceutical composition; and, (e) normal saline solution—76.53% by volume of the total volume of pharmaceutical composition. Each of these numbers is expressed by rounding to the nearest one ten-thousandth of a percent. Furthermore, in the preferred embodiment of the spray form the preservative agent is tocopheryl acetate, the healing agent is aloe barbadensis leaf extract, and the base oil is safflower oil.

The present invention is described above in terms of a preferred illustrative embodiment of a specifically described pharmaceutical composition. Other aspects, features, and advantages of the present invention may be obtained from a study of this disclosure, along with the appended claims. For example, those skilled in the art will recognize that alternative ingredients with the same functional characteristics can be used in carrying out the present invention.

Those skilled will also recognize that the present invention may be used in a variety of circumstances. In some instances, the pharmaceutical composition of the present invention can be used to treat dry-nose condition that is caused by factors other than oxygen treatment. For example, it can treat a type of dry-nose condition that presents itself in climates with little to no humidity, such as the type of climate often encountered while snow skiing or mountain climbing. Additionally, the present invention may be used on other parts of the body that are severely dehydrated and/or cracked. In this capacity, this present invention essentially acts as a moisturizer with ingredients added (1) to kill microorganisms and effectively prevent infection; (2) to enhance wound healing; and, (3) to combat evaporation of the pharmaceutical composition from the skin once applied.

I claim:

1. A pharmaceutical composition for skin and mucosal treatment, comprising:
   a predetermined amount of an antimicrobial component, wherein said antimicrobial component comprises water, propylene oxide, chlorhexidine gluconate 20% w/v, acetic acid, lavender, propylene glycol, hydroxypropyl methylcellulose, polypropylene glycol, and sodium acetate;
   a predetermined amount of preservative agent wherein said preservative agent is tocopheryl acetate;
   a predetermined amount of healing agent wherein said healing agent is aloe barbadensis leaf extract;
   wherein said pharmaceutical composition further comprises a predetermined amount of base oil selected from the group consisting of safflower oil, grape seed oil, and sesame oil; and
   wherein said pharmaceutical composition has a total volume, and wherein said predetermined amount of said antimicrobial component is 90.91% by volume of said total volume, wherein said predetermined amount of preservative agent is 3.03% by volume of said total volume, wherein said predetermined amount of healing agent is 3.03% by volume of said total volume, and wherein said base oil is safflower oil and said predetermined amount of base oil is 3.03% by volume of said total volume.

2. A pharmaceutical ointment for skin and mucosal treatment comprising:
   a predetermined amount of an antimicrobial component, wherein said antimicrobial component comprises water, propylene oxide, chlorhexidine gluconate 20% w/v, acetic acid, lavender, propylene glycol, hydroxypropyl methylcellulose, polypropylene glycol, and sodium acetate;
   a predetermined amount of preservative agent wherein said preservative agent is tocopheryl acetate;
   a predetermined amount of healing agent wherein said healing agent is aloe barbadensis leaf extract; and,
   a predetermined amount of base oil;
   wherein said pharmaceutical ointment has a total volume, and wherein said predetermined amount of said antimicrobial component is 90.91% by volume of said total volume, wherein said predetermined amount of preservative agent is 3.03% by volume of said total volume, wherein said predetermined amount of healing agent is 3.03% by volume of said total volume, and wherein said base oil is safflower oil and said predetermined amount of base oil is 3.03% by volume of said total volume.

* * * * *